(12) United States Patent
Delahaye et al.

(10) Patent No.: US 6,590,650 B1
(45) Date of Patent: Jul. 8, 2003

(54) DEVICE FOR MEASURING THE SIZE OF MOVING PARTICLES, IN PARTICULAR FOR PLUVIOMETRIC MEASUREMENTS

(75) Inventors: Jean-Yves Delahaye, Vanves (FR); Jacques Lavergnat, Pilliers (FR); Jean-Paul Vinson, Meudon (FR); Theodore Danguy, Paris (FR)

(73) Assignee: Centre National de La Recherche Scientififque (CNRS), Paris Cedex (FR)

( * ) Notice: Subject to any disclaimer, the term of this patent is extended or adjusted under 35 U.S.C. 154(b) by 0 days.

(21) Appl. No.: 09/762,600

(22) PCT Filed: Aug. 10, 1999

(86) PCT No.: PCT/FR99/01962
§ 371 (c)(1),
(2), (4) Date: Feb. 20, 2001

(87) PCT Pub. No.: WO00/09987
PCT Pub. Date: Feb. 24, 2000

(30) Foreign Application Priority Data

Nov. 8, 1998 (FR) .............................. 98 10287

(51) Int. Cl.[7] .............................................. G01N 15/02
(52) U.S. Cl. ...................................................... 356/335
(58) Field of Search .................................. 356/335–343; 250/208.1, 574, 214 VT; 318/DIG. 2, 483, 283, 444; 15/DIG. 15; 340/905, 995, 602; 342/26, 115; 347/248, 19, 6; 382/107

(56) References Cited

U.S. PATENT DOCUMENTS

| | | | |
|---|---|---|---|
| 3,962,576 A | * | 6/1976 | Kuhl et al. .............. 250/201.9 |
| 4,263,508 A | * | 4/1981 | Leary et al. ............. 250/358.1 |
| 4,318,180 A | | 3/1982 | Lundovist et al. |
| 4,441,816 A | | 4/1984 | Hencken et al. |
| 4,529,309 A | | 7/1985 | Pettersson et al. |
| 4,895,034 A | | 1/1990 | Poole |
| 4,906,094 A | | 3/1990 | Ashida |
| 5,249,864 A | * | 10/1993 | Fagan et al. ................ 374/110 |
| 5,847,826 A | * | 12/1998 | Fukui et al. ........... 318/DIG. 2 |
| 5,963,315 A | * | 10/1999 | Hiatt et al. .............. 356/237.3 |

FOREIGN PATENT DOCUMENTS

FR         2 293 718          7/1976

* cited by examiner

Primary Examiner—Tu T Nguyen
(74) Attorney, Agent, or Firm—Foley & Lardner

(57) ABSTRACT

The invention concerns a pluviometric device for measuring the diameter of individual raindrops (G) passing through a measuring volume (110), comprising optical transmission means (100), receiving means including at least a sensor receiving at least part of the light derived from at least one transmission means after it has passed through the measuring volume, and processing means (20, 30) which receive the signal at said sensor (120) output and which determine the individual diameter of raindrops. The invention is characterized in that the receiving means include at least two such sensors (124a, 124b) which receive portions of light derived from the transmitting means which are superposed along the general displacement direction of the particles and the processing means (20, 30) operate a correlative processing on the signals at the output of said sensors.

10 Claims, 3 Drawing Sheets

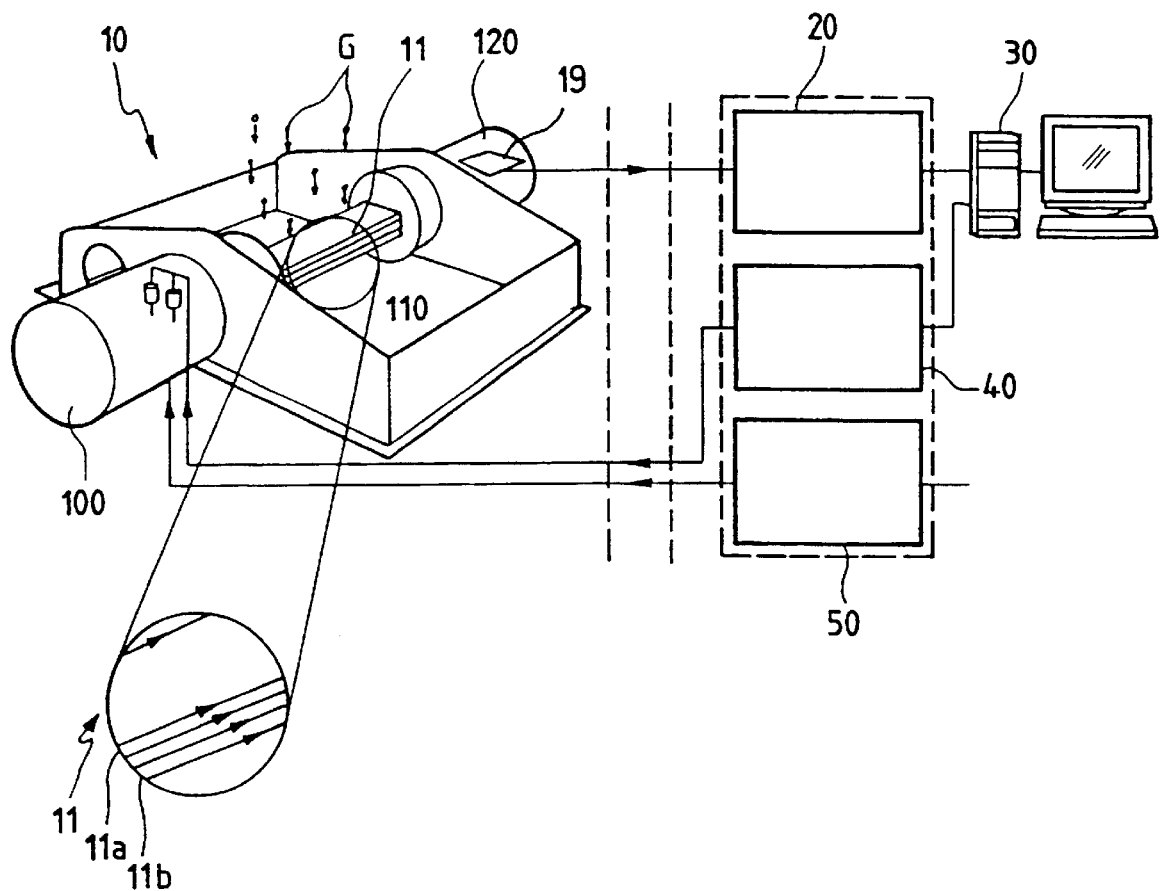

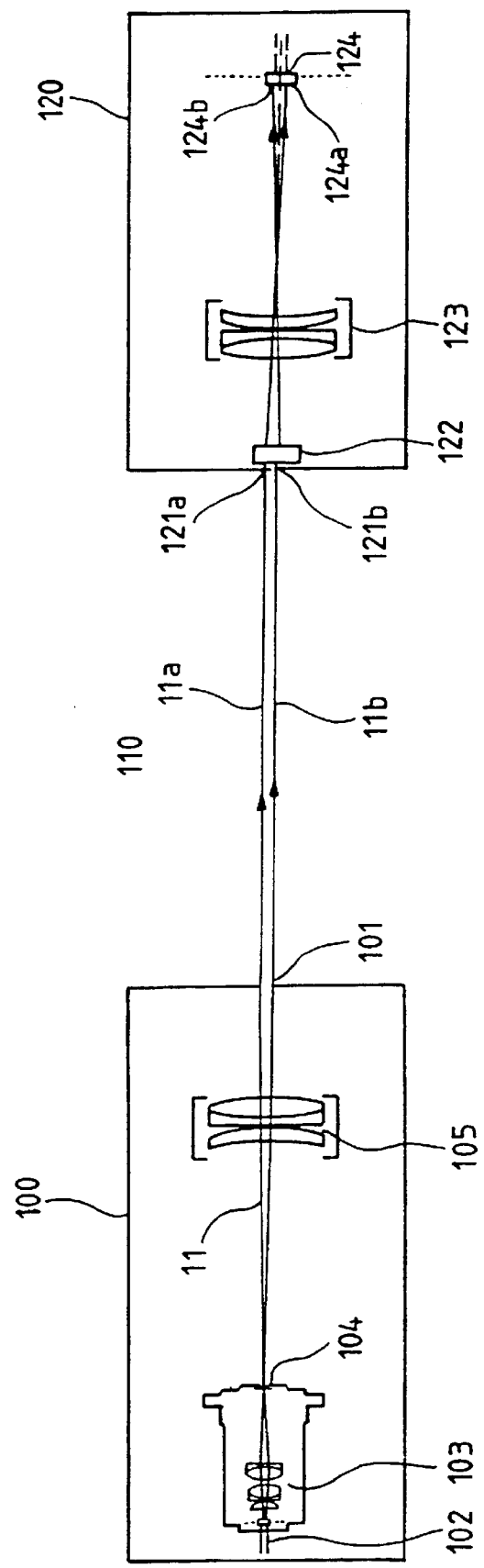
FIG_2

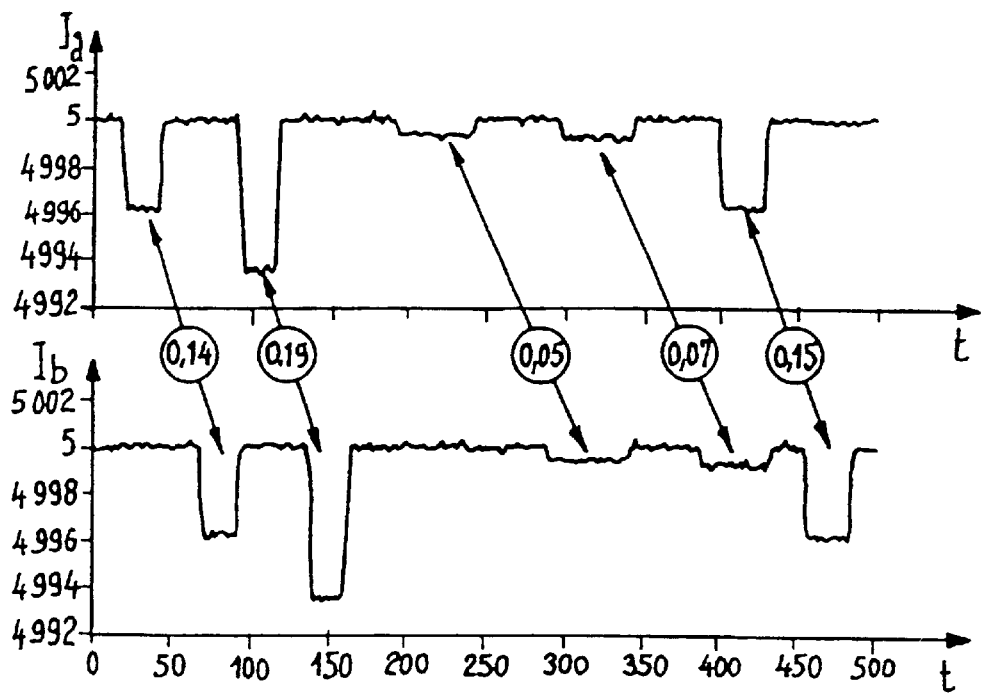
FIG_4
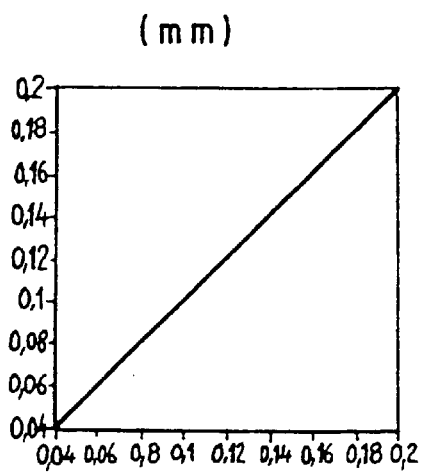
FIG_5
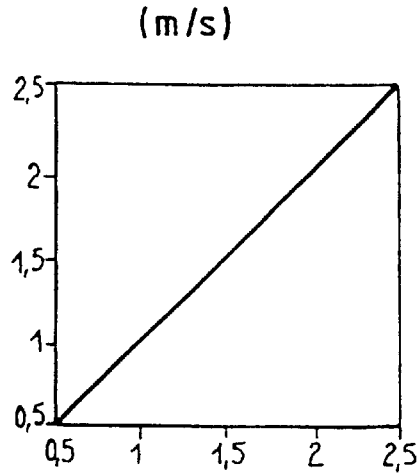
FIG_6

DEVICE FOR MEASURING THE SIZE OF MOVING PARTICLES, IN PARTICULAR FOR PLUVIOMETRIC MEASUREMENTS

CROSS-REFERENCES TO RELATED APPLICATIONS

STATEMENT REGARDING FEDERALLY SPONSORED RESEARCH OR DEVELOPMENT

BACKGROUND OF THE INVENTION

The present invention relates in general to devices for pluviometric measurement by experimental determination of the characteristics of rain, such as the distribution of the sizes, of the velocities of the raindrops falling at a given location and of the times of arrival of the said raindrops.

Pluviometric measuring devices are already known in which the measurements are used for applications such as the real-time modeling of meteorological conditions for air transport, or the forecasting of disturbances caused by rain to telecommunications, in particular to microfrequency waves.

These devices implement various physical principles, the main ones being:

the gathering of raindrops in a container, radar detection, the detection of ultrasound pulses corresponding to the impacts of raindrops on a membrane, the optical detection of the passage of drops through a light beam.

Neither traditional pluviometers (gathering of drops), nor radar detection pluviometers make it possible to obtain individual measurements on the size and the instants of passage of the drops detected.

As far as the other techniques are concerned, although they make it possible to access individual information on each raindrop, they do not make it possible to measure the size of small drops (and in particular to measure diameters of drops of less than 0.5 mm).

This limitation is penalizing:

in respect of the general characterization of rainfall, since the drops with a diameter of less than 0.5 mm constitute a non-negligible proportion of most rainfall spectra, and more particularly with respect to determining the impact of rain on telecommunications, the drops of small diameter having a considerable influence in this area.

An aim of the present invention is to make it possible to produce a device able to retrieve spectra of moving raindrops and the distributions of their times of arrival for drop diameters of less than 0.5 mm.

BRIEF SUMMARY OF THE INVENTION

U.S. Pat. No. 4,529,309 and U.S. Pat. No. 4,318,180 already disclose devices for measuring the diameter of particles passing through a measuring space, comprising optical emission means, reception means comprising at least one photodetector receiving at least part of the light emanating from the emission means after this light has passed through the measuring space, as well as processing means which receive the signal at the output of the sensor, the reception means comprising at least two such photodetectors which receive portions of the light emanating from the emission means, these portions being superposed along the general direction of movement of the particles.

For its part, the invention proposes a pluviometric device characterized in that the device is a pluviometric device for measuring the diameter of raindrops, the processing means comprising means for determining the value to which the intensity of the current at the output of a photodetector decreases during the passage of a drop in front of the photodetector and for deducing therefrom the individual diameter of the drop, the processing means furthermore comprising means for correlating the intensities of current at the output of one and the other of the two photodetectors so as to distinguish the passage of small drops in front of the latter with respect to the noise of the current intensities at the output of the photodetectors.

As will be understood through the description of an exemplary embodiment of the invention, given in the subsequent text, such a device makes it possible to detect moving raindrops of small diameter (down to 0.1 mm or less).

It furthermore makes it possible to determine the velocity of these particles, as well as their direction of movement.

Preferred, but nonlimiting aspects of the device according to the invention are the following:

the emission means comprise a light-emitting diode, as well as optical means for straightening the light emitted by the said diode into a parallel beam;

the reception means comprise at least two slits which are superposed along the general direction of movement of the particles and which separate the light having passed through the measuring space into two portions which are sent respectively to one and the other of the two sensors;

the reception means comprise, downstream of the slits, optical means for concentrating the light received on the sensors;

it comprises means for heating optical means of the reception means;

it comprises means for protecting the sensors from the ambient luminous radiation surrounding the device;

the processing means comprise means for determining the velocity of the raindrops;

the processing means comprise means for determining the instants of arrival of the raindrops;

the processing means comprise means for determining the direction of movement of the raindrops.

BRIEF DESCRIPTION OF THE DRAWINGS

Other aspects, aims and advantages of the present invention will become more apparent on reading the following embodiment, given by way of example and with reference to the appended drawings in which:

FIG. 1 is a diagrammatic representation of an embodiment of the device according to the invention, the said embodiment being intended to perform pluviometric measurements.

FIG. 2 is a diagrammatic representation of the optical chain used in this device, FIGS. 3a to 3c illustrate the time profile of the signals generated by the passage of a raindrop, FIG. 4 depicts two curves of the signals generated by the passage of several raindrops.

FIG. 5 is a graph of the slope Da.

FIG. 6 is a graph of the slope Ma.

DETAILED DESCRIPTION OF THE PREFERRED EMBODIMENTS

The pluviometry measuring device illustrated in FIG. 1 comprises an acquisition module 10 for acquiring signals characteristic of the passage of raindrops G through a measuring space 110, as well as various means referenced 20, 30, 40 and 50 in FIG. 1, for the control of the said module and the processing of the signals which it makes it possible to acquire.

The acquisition module 10 comprises an emission box 100 which generates a parallel light beam 11 extending along a plane horizontal sheet, so as to intercept the raindrops at an angle of close to 90°.

This beam exits the emission box through an elongated horizontal slit (not represented in the figure). This slit has a total height of 8 mm, of which 6 mm correspond to the useful thickness of measurement; 1 mm as a safeguard at the top, 1 mm as a safeguard at the bottom, so as to take account of the mechanical fluctuations between the emission box and reception box. It has a total width of 42 mm, of which 40 mm is the useful width for the measurement, 1 mm as a safeguard on the left, 1 mm as a safeguard on the right. The wavelength of the beam 11 is close to that of infrared.

Having exited the emission box, the beam 11 propagates through the measuring space 110—this being an open space which the acquisition module 10 exhibits in its middle part and through which raindrops may fall.

The raindrops therefore pass through the beam 11, in this measuring space 110.

The beam is then received in a reception box 120, which at its inlet exhibits two vertically superposed horizontal rectangular slits which separate the said beam into two portions which are concentrated on two photodiodes by optical means of the said box 120.

Thus, the beam 11 which passes through the measuring space 110 may be regarded as consisting of two superposed active portions (referenced 11a and 11b in FIG. 1) separated by an intermediate portion whose information is not used.

While falling, the raindrops pass successively through the upper active portion 11a, the intermediate portion, then the lower portion 11b, the drops passing through the three sheets of beam at an angle substantially equal to 90° with respect to the planes of the said sheets.

FIG. 2 is a representation of the optical elements of the acquisition module 10, the elements constituting an optical chain for emitting the beam 11, and separately gathering the light of the active portions of beam 11a, 11b after it has passed through the measuring space 110.

The emission box 100 comprises a light source 102 which is a light-emitting diode.

The light emitted by this diode 102 is received by a first assembly 103 consisting of an aplanatic meniscus and of two opposed doublets.

As a variant, the source 102 can be a laser.

This assembly 103 concentrates the light from the source 102 onto a source hole 104. The beam 11 emanating from the source hole 104 is then straightened by a triplet 105 so as to constitute a horizontal parallel beam, then it leaves the emission box 100 through the rectangular slit alluded to above and which has been referenced 101 in FIG. 2.

On exiting the emission box 100, the beam 11 passes through the measuring space 110 and enters the box 120 via the two horizontal rectangular entrance slits exhibited by the box 120. These slits have been referenced 121a and 121b. They are of dimensions 40×2 mm and are separated by 2 mm.

After having entered the box 120, the light of the two active portions 11a and 11b is concentrated by a prism 122 and a triplet 123 onto the two photodiodes 124a and 124b respectively of a double photoelectric receiver 124.

Moreover, as illustrated in FIG. 1, the pluviometry measuring device comprises in association with the acquisition module:

an interface 19 which converts the analog signals emanating from the receiver 124 into serial digital signals;

an interface 20 linked to the acquisition module 10. This interface transforms the digital signals emanating from the interface 19 into parallel signals;

a management computer 30 linked to the interface 20 so as to recover the said digital signals, process these signals so as to deduce therefrom information on the rain passing through the measuring space of the acquisition module, display and store this information, a calibration control module 40 interconnected between the computer 30 and the acquisition module 10. This calibration control module receives instructions from the management computer and transmits calibration signals to the module 10 accordingly, a power supply 50 linked to the acquisition module.

The intensity level of the light emitted by the box 100 being regardable as constant over the duration of the measurement, the passage of a drop through one of the two active portions of beam 11a and 11b brings about a reduction in the luminous intensity concentrated on the photodiode corresponding to this portion of beam.

Represented in FIG. 3a is the descent of a raindrop G through the beams 11a and 11b, and represented in the graphs of FIGS. 3b and 3c are the modifications to the luminous intensities $I_a$ and $I_b$ received by the photodiodes 124a and 124b, during this descent.

In the absence of raindrops within the measurement area, the intensities $I_a$ and $I_b$ are the reference values $I_{Oa}$ and $I_{Ob}$ corresponding to the entire light of the sheets of beams 11a and 11b respectively.

When now a drop G enters the vertical thickness of the upper beam sheet 11a, the value of $I_a$ decreases according to a downward slope Da during a time interval $\Delta T_{Da}$, until the drop is completely within the thickness of the portion 11a and until $I_a$ stabilizes at a value $I_{Ga}$.

The drop G continuing its descent, it leaves the thickness of the sheet 11a and $I_a$ increases during $\Delta T_{Ma}$ from $I_{Ga}$ to $I_{Oa}$, according to an upward slope Ma.

When the drop G enters the thickness of the lower beam sheet 11b, the value of $I_b$ decreases from $I_{Ob}$ to $I_{Gb}$ during the time interval $\Delta T_{Gb}$. Finally, when the drop leaves the lower edge of the beam sheet 11b, $I_b$ regains its reference value $I_{Ob}$ via a variation during $\Delta T_{Mb}$.

The quantity of light absorbed or deflected by the drop depends on the size of the said drop, it is possible to link the values $I_{Gb}$ and $I_{Ga}$ to a characteristic dimension of the drop G, for example its equivalent diameter which is the diameter which a spherical drop would have if it did not experience the aerodynamic loads due to its descent, and the resulting deformations.

Although the establishing of such a relation between the luminous intensity received and the size of the drop is known per se (see for example patent FR 2 293 718), the use according to the invention of two superposed beams each providing a signal makes it possible advantageously to perform, by virtue of the processing means of the management computer 30, a fine correlation of the signals $I_a$ and $I_b$.

An exemplary recording of the signals $I_a$ and $I_b$ has been plotted in the graphs of FIG. 4.

It may be noted that each signal comprises noise which rules out the reliable detection of small drops.

The correlation processing implemented by the management computer on the signals $I_{Ga}$ and $I_{Gb}$ transmitted by the two beams during the passage of one and the same drop G through the measuring space allows the accuracy of the measurements to be improved as substantially by characterizing the drops whose equivalent diameter can have a value as small as around 0.1 mm.

The correlation processing can be of any type. It consists for example of a correlation processing by fast Fourier transform (FFT according to the terminology of the person skilled in the art).

It will be noted that the foregoing description dealt with drops of a diameter of less than 2 mm. However, this measurement principle applies equally to particles of a greater diameter, provided that the processing takes account of the fact that the occulted surface area is proportional to the intersection between the surface area of the slit and the surface area of the particle.

In this FIG. 4, the circled values are the equivalent radii of the drops passing through the beams (in mm). As has been stated, these values emanate from the processing means associated with the management computer 30, the said processing means implementing correlations between the signals received by the two photodiodes of the device.

Furthermore, by employing two beams it is possible to reduce the thickness of the said beams and to thus decrease the probability that two different drops falling together will generate a signal appearing to be a single signal as they pass through the beam.

Moreover, the processing means of the device also make it possible to deduce slopes Da and Ma, shown in FIGS. 5 and 6 respectively, as well as the duration of residence of a drop in a beam, the velocity of the decent of the drops.

A further advantage of the device according to the invention is that by employing two signals it is possible to determine the direction of movement of the drops unambiguously, which was not the case with the devices of the prior art such as that described in patent FR 2 293 718. This advantage is not negligible insofar as numerous raindrops pass through the device upwards from bottom to top, carried by convection currents.

According to a variant which is not represented in the figures, the two boxes of the module 10 comprise means for heating the optical elements, linked to the supply 50 of FIG. 1. In this variant, the heating means make it possible to reduce the effects of condensation on the optics.

According to another variant of the invention, there are provided means such as opaque flaps surrounding the two slits of the box 120 to prevent the ambient radiation from disturbing the measurement of the light of the beam portions 11a and 11b and to protect the elements of the box 120 from water splashes in the case of applications to pluviometry measurement. When implementing the device according to the invention, the acquisition module is placed in situ in the flow of drops (or of particles) to be characterized.

The other elements of the device can be clustered together in a processing zone protected in the case of pluviometry measurements.

For the calibration of the device, it is possible according to the invention to partially and alternately occult one or the other of the lateral edges of the two beam portions 11a and 11b, by means of vertical rods which can be interposed in the measuring space 110 in the path of beams.

The operator knowing the quantity of light which should be intercepted by the rod, it is possible to move the rod within the measuring space so as to detect any spatial inhomogeneities in the distribution of light from the beams.

Such inhomogeneities may be due to pollution, or to a foreign body (insect, etc.) in the measuring space. The movement of the rods is controlled by the calibration control module 40.

According to another characteristic of the invention, it is possible to provide means for modulating the light emitted by the light source 102. Modulation of the emission of light makes it possible on the one hand to increase the signal/noise ratio of the signals $I_a$ and $I_a$ and on the other hand to perform fast measurements of the level of ambient light by comparison of the signals received during the light pulses and between these pulses.

Again as a variant, it is possible to place the source 102 directly in the position of the source hole 104. The assembly 103 and the source hole 104 are then dispensed with. The source 102 used is then the model referenced HE8404SG from Hitachi. The other elements remain unchanged.

What is claimed is:

1. Pluviometric device for measuring the diameter of liquid droplets passing though a measuring space, comprising:
    a) optical emission means for emanating light;
    b) reception means for receiving light emanating from said optical emission means after said light has passed through said measuring space, wherein said reception means comprises:
        i) a first sensor that produces a first output signal in response to receiving a first portion of said light, and
        ii) a second sensor that produces a second output signal in response to receiving a second portion of said light; wherein the passage of a droplet through said first and said second portions of light results in a change in luminous intensity at said first and said second sensors, and wherein said first and said second output signals change their values in correspondence with said change in luminous intensity; and
    c) processing means for processing said output signals, wherein said processing means determines the diameter of said droplet by correlating said first output signal and said second output signal.

2. Pluviometric device according to claim 1, wherein said optical emission means comprises a light-emitting diode and optical means for straightening the light emitted by said light-emitting diode into a parallel beam.

3. Pluviometric device according to claim 1, wherein said reception means further comprises at least two slits which are superposed along the general direction of movement of the droplets and wherein said slits separate the light into said first and second portions after said light has passed through said measuring space.

4. Pluviometric device according to claim 3, wherein said reception means further comprises, downstream of said slits, optical means for concentrating said first and second portions on said first and second sensors, respectively.

5. Pluviometric device according to claim 4, further comprising means for heating said optical means.

6. Pluviometric device according to claim 1, further comprising means for protecting said first and second sensors from ambient luminous radiation.

7. Pluviometric device according to claim 1, wherein said processing means further comprises means for determining the velocity of the droplets.

8. Pluviometric device according to claim 1, wherein said processing means further comprises means for determining the instants of arrival of the droplets.

9. Pluviometric device according to claim 1, wherein said processing means further comprises means for determining the direction of movement of the droplets.

10. Pluviometric device for measuring the diameter of a raindrop passing though a measuring space, comprising:

a) optical emission means for emanating light;
b) reception means for receiving light emanating from said optical emission means after said light has passed through said measuring space, wherein said reception means comprises:
   i) a first photodetector that produces a first output current in response to receiving a first portion of said light, and
   ii) a second photodetector that produces a second output current in response to receiving a second portion of said light, and
   wherein the passage of said raindrop through said first and said second portions of light results in a change in luminous intensity at said first and said second photodetectors, and wherein said first and said second output currents change their values in correspondence with said change in luminous intensity; and
c) processing means for processing said first and said second output currents, wherein said processing means correlates said first output current and said second output current to produce a correlated signal, and wherein said processing means filter determines the diameter of said raindrop from said correlated signal.

* * * * *